United States Patent
Mahesh

(10) Patent No.: US 7,961,921 B2
(45) Date of Patent: Jun. 14, 2011

(54) SYSTEM AND METHOD FOR MEDICAL DIAGNOSIS AND TRACKING USING THREE-DIMENSIONAL SUBTRACTION IN A PICTURE ARCHIVING COMMUNICATION SYSTEM

(75) Inventor: Prakash Mahesh, Schaumburg, IL (US)

(73) Assignee: General Electric Company, Schenectady, NY (US)

( * ) Notice: Subject to any disclaimer, the term of this patent is extended or adjusted under 35 U.S.C. 154(b) by 1089 days.

(21) Appl. No.: 11/236,353

(22) Filed: Sep. 27, 2005

(65) Prior Publication Data

US 2007/0071294 A1 Mar. 29, 2007

(51) Int. Cl.
- G06K 9/00 (2006.01)
- A61B 5/05 (2006.01)
- A61B 6/00 (2006.01)

(52) U.S. Cl. ...................................... 382/128; 600/427

(58) Field of Classification Search .................. 382/103, 382/128–132, 293–295; 128/922; 250/455; 356/39; 377/10; 600/407, 411, 427

See application file for complete search history.

(56) References Cited

U.S. PATENT DOCUMENTS

| | | | | |
|---|---|---|---|---|
| 5,647,360 A | * | 7/1997 | Bani-Hashemi et al. | 600/425 |
| 6,023,495 A | * | 2/2000 | Adler et al. | 378/4 |
| 6,678,399 B2 | | 1/2004 | Doi et al. | |
| 6,999,811 B2 | * | 2/2006 | Koppe et al. | 600/426 |
| 7,106,891 B2 | * | 9/2006 | Wyman et al. | 382/128 |
| 7,171,257 B2 | * | 1/2007 | Thomson | 600/427 |
| 7,274,810 B2 | | 9/2007 | Reeves et al. | |
| 7,289,651 B2 | * | 10/2007 | Vining et al. | 382/128 |
| 7,386,156 B2 | * | 6/2008 | Hornegger | 382/130 |
| 2003/0026758 A1 | * | 2/2003 | Baker | 424/9.1 |
| 2003/0099388 A1 | | 5/2003 | Doi et al. | |
| 2004/0258289 A1 | * | 12/2004 | Hornegger | 382/130 |
| 2005/0002546 A1 | * | 1/2005 | Florent et al. | 382/128 |
| 2005/0053267 A1 | * | 3/2005 | Mostafavi | 382/128 |
| 2005/0084178 A1 | | 4/2005 | Lure et al. | |

OTHER PUBLICATIONS

Aylward S, Weeks S, Bullitt E Analysis of the parameter space of a metric for registering 3D vascular images. MICCAI, 2208 LNCS, Springer-Verlag, 2001. pp. 932-939.*
Bullitt, E.; Aylward, S.R., "Analysis of time-varying images using 3D vascular models," Applied Imagery Pattern Recognition Workshop, AIPR 2001 30th , vol., No., pp. 9-14, Oct. 1-12, 2001.*
Sung et al, "Digital subtraction CT angiography based on efficient 3D registration and refinement" Computerized Medical Imaging and Graphics Oct. 2004 (vol. 28, Issue 7, pp. 391-400).* Miyazaki et al, Non-contrast-enhanced MR Angiography of Peripheral Arteries Using ECG-gated Three-dimensional FASE, Journal of Magnetic Resonance Imaging 12:776-783 (2000).*
Schaefer-Prokop, et al., "New imaging techniques in treatment guidelines for lung cancer," Eur Respir J 2002; 19: Suppl. 35, 71s-83s.
Katsumi, et al., "Non-contrast-enhanced MR Angiography of Peripheral Arteries Using ECG-gated Three-dimensional FASE," Japanese Journal of Diagnostic Imaging, vol. 24, No. 9, Abstract, 2004.

* cited by examiner

Primary Examiner — Vu Le
Assistant Examiner — Andrae S Allison
(74) Attorney, Agent, or Firm — McAndrews, Held & Malloy, Ltd.; Michael A. Dellapenna

(57) ABSTRACT

Certain embodiments of the present invention provide for a system for medical diagnosis and tracking. In an embodiment, a medical diagnosis and tracking system includes one or more medical imaging devices adapted to create one or more current images. The medical diagnosis and tracking system also includes a historical images archive adapted to storing the one or more current images and/or one or more historical images. The system also includes a three-dimensional subtraction application adapted to create one or more three-dimensional subtracted images by performing three-dimensional subtraction on the one or more current images and the one or more historical images. The medical diagnosis and tracking system also includes a Picture Archiving Communication System (PACS) workstation adapted to display the one or more three-dimensional subtracted images.

16 Claims, 2 Drawing Sheets

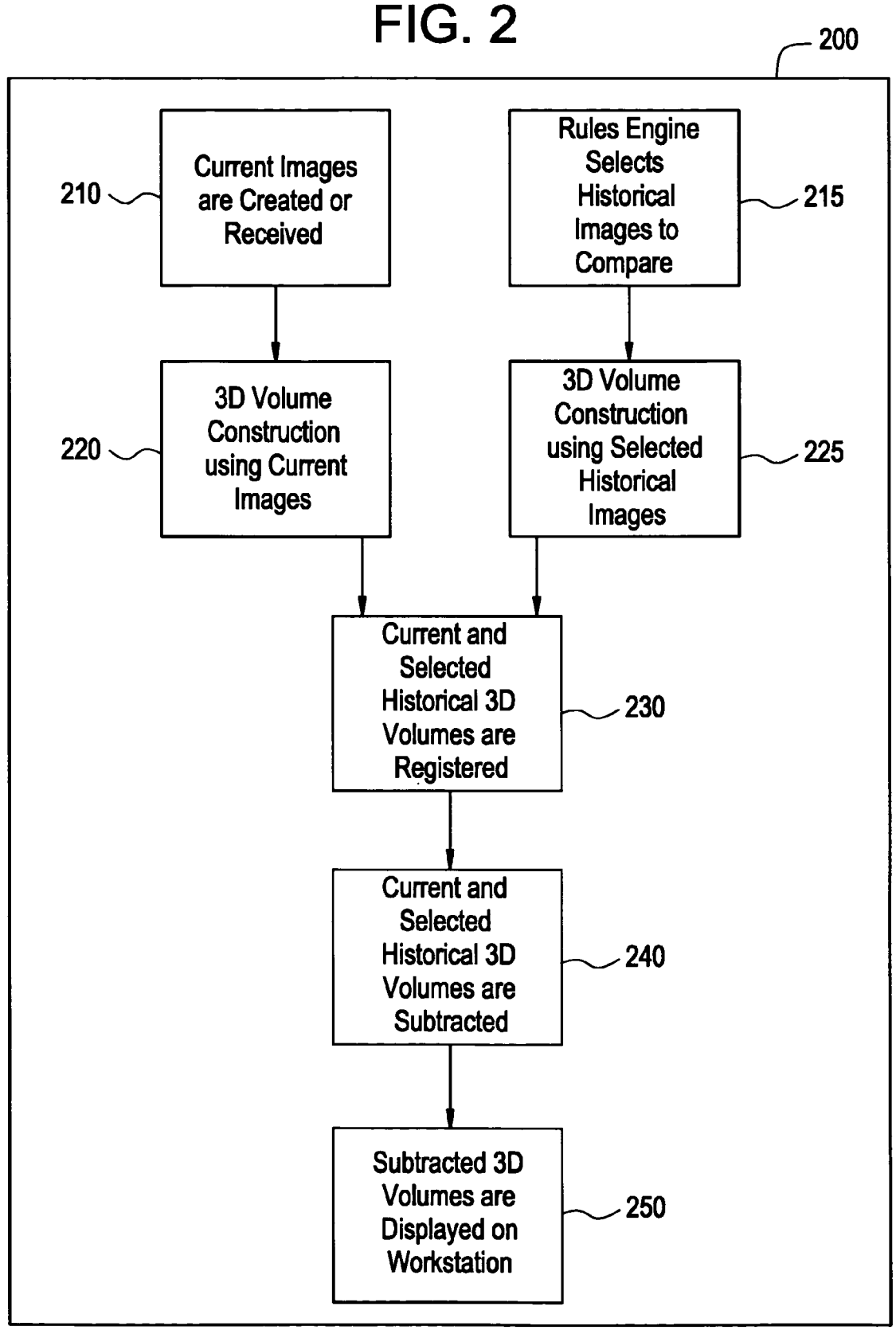

SYSTEM AND METHOD FOR MEDICAL DIAGNOSIS AND TRACKING USING THREE-DIMENSIONAL SUBTRACTION IN A PICTURE ARCHIVING COMMUNICATION SYSTEM

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF INVENTION

Embodiments of the present system and method relate generally to diagnostic imaging of patients in a healthcare setting. Particularly, certain embodiments relate to providing improved diagnosis and tracking of changes to tumors in a patient.

In the past, healthcare facilities relied on film-based imaging modalities in which a diagnostic image of a patient was captured on film. Due to the increasing capability of computer technology, healthcare facilities now often employ certain types of digital diagnostic imaging modalities, such as computer tomography (CT), magnetic resonance imaging (MRI), ultrasound imaging, X-ray imaging, and nuclear medicine imaging. Digital diagnostic imaging modalities in a healthcare facility are often linked to a Picture Archiving and Communication System (PACS), either directly or via a network.

With the film-based imaging of the past, a radiologist may evaluate a series of image captured on film. This process of evaluating a series of film images was often time-consuming and cumbersome. Now, a radiologist or other user may instead evaluate a series of digital diagnostic images on a computer workstation. A radiologist may also need to perform advanced post-processing of images. One type of advanced post-processing is three-dimensional image creation. Three-dimensional images may be created, for example, from a series of two dimensional image "slices" that are "stacked" to form a volume. The resulting three-dimensional volumetric image may allow a radiologist or other user to better diagnose a complex medical issue, such as the status of a tumor.

Another type of advanced post-processing is three-dimensional subtraction. Basically, three-dimensional subtraction allows a radiologist or other practitioner to view the differences between two or more images. A three-dimensional image subtraction application does this by aligning the images to be compared using image registration techniques, and subtracting out characteristics which are the same in each image (such as bone). The resulting three-dimensional subtracted image may allow a radiologist or other practitioner to diagnose or track medical conditions, such as changes in a tumor.

For simple evaluation of digital diagnostic images, a user may evaluate images as they are displayed on a PACS. However, since current PACS do not perform advanced post-processing of images, any advanced diagnosis may have to take place on a separate workstation from the PACS. A system and method for medical diagnosis and tracking using a PACS would improve the efficiency in which a practitioner may access, view, and perform advanced post-processing on one or more images. Thus, there is a need for a system and method for improving workflow in a healthcare environment using three-dimensional subtraction in a PACS to diagnose and track a patient's medical condition.

BRIEF SUMMARY OF THE INVENTION

Certain embodiments of the present invention may provide for a system for medical diagnosis and tracking. In an embodiment, a medical diagnosis and tracking system may include one or more medical imaging devices adapted to create one or more current images. The medical diagnosis and tracking system may also include a historical images archive adapted to storing the one or more current images and/or one or more historical images. The system may also include a three-dimensional subtraction application adapted to create one or more three-dimensional subtracted images by performing three-dimensional subtraction on the one or more current images and the one or more historical images. The medical diagnosis and tracking system may also include a Picture Archiving Communication System (PACS) workstation adapted to display the one or more three-dimensional subtracted images.

Certain embodiments of the present invention may provide for a method for medical diagnosis and tracking. In an embodiment, a method for medical diagnosis and tracking may include receiving one or more current medical images. The method may also include selecting one or more historical images. In addition, the method may include generating one or more current three-dimensional volume images using one or more current medical images and generating one or more historical three-dimensional volume images using the one or more historical images. The method may also include registering the one or more current three-dimensional volume images and the one or more historical three-dimensional volume images using image registration techniques. The method for medical diagnosis and tracking may also include constructing one or more three-dimensional subtracted images. Additionally, the method may include displaying the one or more three-dimensional subtracted images on a Picture Archiving Communication System (PACS) workstation.

Certain embodiments of the present invention may provide for a computer-readable storage medium including a set of instructions for a computer. The set of instructions may include a receiving routine for receiving one or more current images from a medical imaging device. The set of instructions may also include a selection routine for selecting one or more historical images. In addition, the set of instructions may include a generation routine for generating one or more current three-dimensional volume images using the one or more current images and generating one or more historical three-dimensional volume images using the one or more historical images. The set of instructions may also include a registration routine for registering the one or more current three-dimensional volume images and the one or more historical three-dimensional volume images using image registration techniques. Additionally, the set of instructions may include a construction routine for constructing one or more three-dimensional subtracted images. The set of instructions may also include a display routine for displaying the one or more three-dimensional subtracted images on a Picture Archiving Communication System (PACS) workstation.

BRIEF DESCRIPTION OF SEVERAL VIEWS OF THE DRAWINGS

FIG. 2 illustrates a flow diagram for a method for medical diagnosis and tracking in accordance with an embodiment of the present invention.

Figure 1:
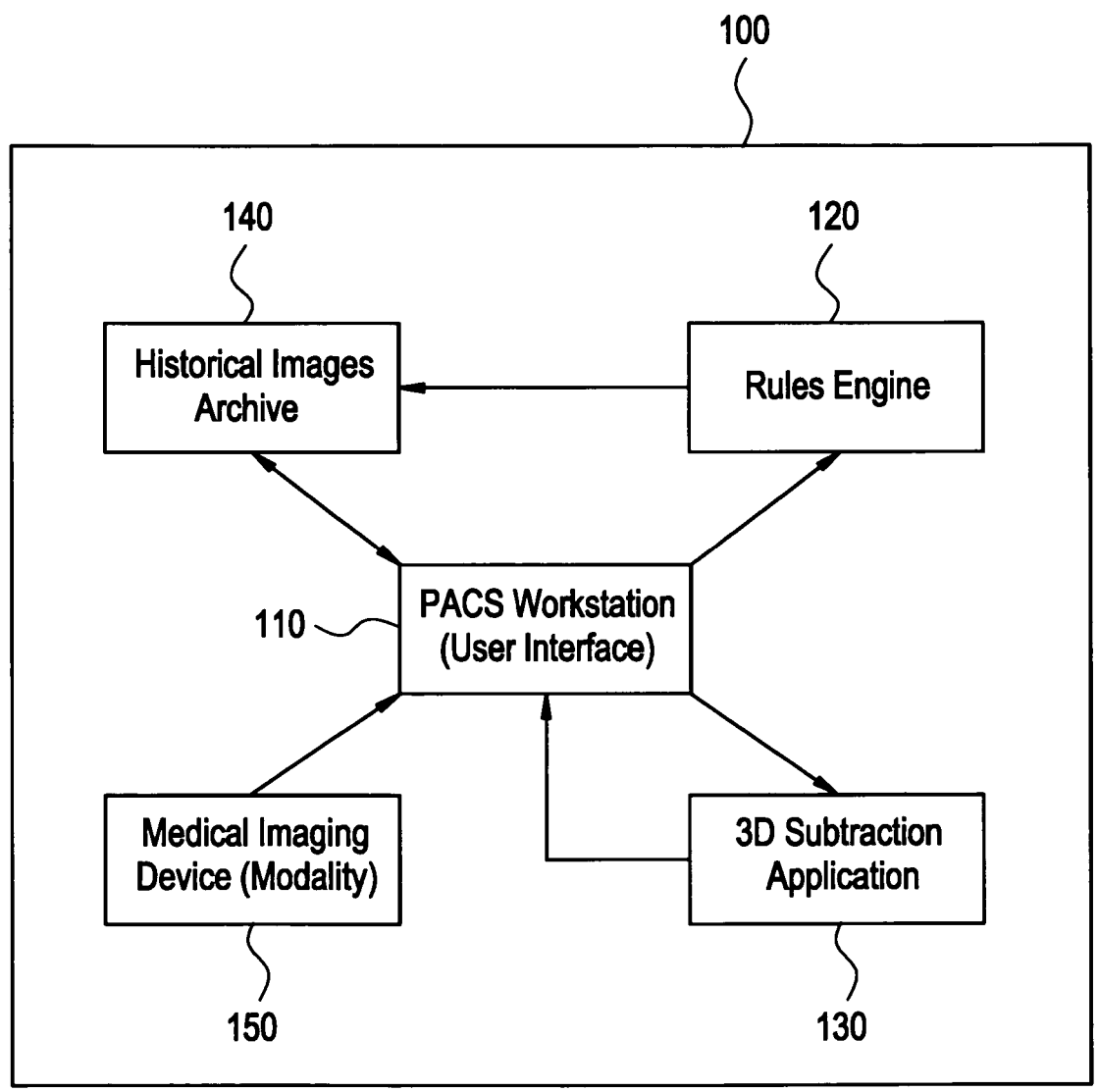
FIG. 1 illustrates a medical diagnosis and tracking system used in accordance with an embodiment of the present invention.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentality shown in the attached drawings.

DETAILED DESCRIPTION OF THE INVENTION

FIG. 1 illustrates a medical diagnosis and tracking system 100 used in accordance with an embodiment of the present invention. The system 100 includes a Picture Archiving Communication System (PACS) workstation 110, a rules engine 120, a three-dimensional (3D) subtraction application 130, a historical images archive 140, and a medical imaging device 150. The components of the system 100 may communicate via wired and/or wireless connections on one or more processing units, such as computers, medical systems, storage devices, custom processors, and/or other processing units. In an embodiment, the components of the medical diagnosis and tracking system 100 are integrated into a single unit, or may be integrated in various forms.

The system 100 may be used to provide a solution for accessing, performing advance post-processing using a three-dimensional subtraction application (or other advanced post-processing application), and viewing one or more images on a Picture Archiving Communication System (PACS) workstation 110 to diagnose and track a patient's medical condition. For example, a radiologist, cardiologist, technician, or other healthcare personnel that uses medical imaging technology often uses three-dimensional post processing generation applications to generate post-processed images based on images created in a current and/or previous examination. These post-processed images can offer views of the anatomy that assist a radiologist or other doctor in visualizing and detecting abnormalities. Further, a radiologist, cardiologist, technician, or other healthcare personnel may desire information accessible on a PACS, such as historical images, for example. In an embodiment, the system 100 may integrate the use of advanced post-processing applications (such as a three-dimensional subtraction application 130) with the capabilities and functionality of PACS, allowing a user to efficiently view, access, and alter images on a single workstation or system.

In an embodiment, a medical imaging device 150 is used to capture a current image or set of images of a patient. The medical imaging device 150 may use X-ray, computer tomography (CT), magnetic resonance imaging (MRI), ultrasound, nuclear medicine imaging techniques, or other imaging techniques for example. The operation of the medical imaging device 150 may be controlled via a PACS workstation 110 or it may operate independently, among other things. The images created by the medical imaging device 150 may be sent to an attached (or linked) PACS 110 workstation.

In an embodiment, a historical images archive 140 is used to store images. The historical images archive 140 is accessible to the PACS workstation 110. For example, a user of the PACS workstation 110 may retrieve images stored in the historical images archive 140 to view or perform post-processing on selected images. In addition, among other things, the historical images archive 140 may provide selected images to the PACS workstation 110 at the direction of the rules engine 120. The PACS workstation 110 may save current images to the historical images archive 140. The PACS workstation 110 may also save post-processed images (including three-dimensional volumes and three-dimensional subtracted images, among other things) to the historical images archive 140. The historical images archive 140 may be integrated into the PACS workstation 110 and/or it may be an independent database accessible to the PACS workstation 110 (directly or through a network, for example).

In an embodiment, a systems manager or user creates rules for the system 100, which are stored in the rules engine 120 and may relate to parameters for selecting images from the historical images archive 140 to compare with current images captured by the medical imaging device 150, for example. For example, in a radiology department of a hospital, a system administrator or user may create a rule stating that historical images related to a current image or set of current images captured by the medical imaging device 150 for the same patient, using the same modality, on the same body part (e.g. lung, heart, brain, etc.) are to be selected and forwarded on to the PACS workstation 110 for comparison and post-processing applications (e.g. three-dimensional subtraction). Rules may be created based on a patient, time period, examination type, disease type, system type, etc. Rules may be predefined and/or created dynamically by the practitioner. The rules engine 120 may be integrated into the PACS workstation 110 and/or it may be an independent engine accessible to the PACS workstation 110 (directly or through a network, for example). Rules may be manually configured by a user and/or automatically generated via software. Alternatively, a user may choose not to use the rules engine 120 and may manually select an image (or set of images) to compare from the historical images archive 140.

In an embodiment, a three-dimensional subtraction application 130 is used to create a three-dimensional subtracted image (or set of images) by subtracting common image data (e.g. bone) from two or more compared three-dimensional images. For example, a radiologist or other medical personnel may want to track changes in a patient's tumor. The radiologist or other medical personnel may use the medical imaging device 150 to capture a current image of the tumor. Then the current image of the tumor may be used with a historical image of the tumor in a three-dimensional subtraction application 130. The three-dimensional subtraction application 130 may create an image (or set of images) based on the differences between the current image (or set of images) and the historical image (or set of images). In another example, a radiologist or other healthcare professional may use a medical imaging device 150 to capture an image (or set of images) without contrast and then capture a second image (or set of images) using contrast. Then the image without contrast and the image with contrast may be used by a three-dimensional subtraction application to create a subtracted image (or set of images) displaying the difference between the image (or set of images) without contrast and the image (or set of images) with contrast.

In an embodiment, before three-dimensional subtraction takes place, the images to be compared to create a three-dimensional subtracted image (or set of images) may be used to generate three-dimensional volumes (if the images to be compared are two-dimensional images, for example). Three-dimensional images may be created, for example, from a series of two dimensional image "slices" that are "stacked" to form a volume. The three-dimensional volume construction may be a function of the three-dimensional subtraction application or there may be a separate application to generated the three-dimensional volumes, for example.

In an embodiment, before three-dimensional subtraction takes place, image registration techniques are used to properly convert and align three-dimensional volume images into the appropriate format. Image registration techniques are used to identify and map points in an image 140 to a reference coordinate system and/or other image 130, for example. Image registration techniques may use extrinsic methods (e.g. artificial objects attached to the patient), intrinsic methods (e.g. patient generated image content), and non-image based methods (e.g. calibrating the equipment used in taking the images), among other things. Examples of intrinsic methods used for image registration techniques may include landmark based techniques (e.g. salient or geometrical), segmentation based techniques (e.g. rigid or deformable model), and voxel based techniques (e.g. operates directly on image gray values), among other things. The one or more image registration technique used to automatically generate post-processed images depend on the examination performed and the radiologist or other healthcare professionals choice (or the default in the post processing engine 170).

In an embodiment, a Picture Archiving Communication System (PACS) workstation 110 interacts with the medical imaging device 150, the rules engine 120, the historical images archive 140, and the three-dimensional subtraction application 130, among other things, to collect and display sets of images useful to a radiologist or other healthcare professional for diagnosing and tracking medical conditions. The PACS workstation 110 may also be used as a user interface. For example, a user of the PACS workstation 110 may control the medical imaging device 150. The user may access historical images from the historical images archive 140. Further, the user may view images and/or perform post-processing on images using the PACS workstation 110 and integrated viewing software and/or post-processing applications (such as the three-dimensional subtraction application 130). A user may set up rules for the rules engine 120 so that the rules engine 120 may automatically carry out tasks upon conditions specified by the user. The rules engine 120, historical images archive 140, three-dimensional subtraction application 130, medical imaging device 150, and PACS workstation 110 may be a single system (or any combination may be a single system) or the PACS workstation 110 may have access to any or all of the components via wired or wireless connections, for example.

In operation, a radiologist or other healthcare professional may perform an examination using a medical imaging device 150. The current image or set of current images captured by the medical imaging device 150 may be sent to the PACS workstation 110. The PACS workstation 110 recognizes the received current image or set of current images, saves the current image or set of current images to the historical images archive 140, and directs the rules engine 120 associated with the PACS workstation 110 to either perform the rules set up previously by a system administrator, user, or default setting, for example, or to perform under new rules set up by a user, among other things. For example, the rules previously set up by a user or system administrator may state that historical images related to a current image or set of current images captured by the medical imaging device 150 for the same patient, using the same modality, on the same body part (e.g. lung, heart, brain, etc.) are to be selected and forwarded on to the PACS workstation 110 for comparison and post-processing applications (e.g. three-dimensional subtraction). The rules engine, as stated by the rules, would direct the historical images archive 140 to forward historical images related to the current image using the same modality as the current image, on the same body part as the current image to the PACS workstation 110. Alternatively, a user may forego using the rules engine and instead, may manually select the image (or set of images) to be compared from the historical images archive 140. The PACS workstation 110 may send the current image (or set of current images) and the selected historical image (or set of selected historical images) to the three-dimensional subtraction application 130. The three-dimensional subtraction application 130 may perform three-dimensional volume construction on the current and selected historical images. The three-dimensional subtraction application 130 may also perform image registration techniques prior to performing three-dimensional subtraction on the three-dimensional volume images. Alternatively, the PACS workstation 110 may use a separate three-dimensional volume construction post-processing application to construct the three-dimensional volumes and/or the PACS workstation may use a separate image registration application to register the three-dimensional volumes before sending the volumes to the three-dimensional subtraction application 130 for further post-processing. The three-dimensional subtraction application 130 may perform three-dimensional subtraction on the three-dimensional volumes generating a three-dimensional subtracted image (or set of images). The three-dimensional subtracted image (or set of images) may then be forwarded to the PACS workstation 110 to be saved to the historical images archive 140 and displayed on the PACS workstation 110 for the user, for example.

FIG. 2 illustrates a flow diagram for a method 200 for medical diagnosis and tracking in accordance with an embodiment of the present invention.

First, at step 210, current images are created using a medical imaging device 150. The current images may be created using X-ray, computer tomography (CT), magnetic resonance imaging (MRI), ultrasound, nuclear medicine imaging techniques, or other imaging techniques, for example. The current images created by the medical imaging device 150 may be sent to an attached (or linked) PACS 110 workstation. The PACS workstation 110 may manually receive the current images created by the medical imaging device 150 or a software receiving routine may be implemented to automatically receive the current images, among other things.

At step 215, the rules engine uses rules to select historical images to compare to with the current images created by the medical imaging device 150. The rules may be defined for a particular patient, for a particular user or group of users (e.g., surgeons, radiologists, cardiologists, etc.), for a particular use or group of uses (e.g., image-guided surgery, radiology reading, structured reporting, examination, etc.), and/or for a particular modality (e.g., x-ray, ultrasound, magnetic resonance imaging, etc.), for example. Rules may be defined by software (e.g. historical image selection routine), by a user, and/or by a system administrator, for example. New rules may be created, and/or existing rules may be modified at any time by accessing and storing the new or modified rule in the rules engine 120. The rules are utilized by the rules engine 120 to determine. Alternatively, a user may choose not to use the rules engine and may manually select an image (or set of images) to compare from the historical images archive 140.

Then, at steps 220 and 225, three-dimensional volume images are constructed using the current images and the selected historical images. The three-dimensional volumes may be created by stacking a series of two-dimensional image slices, for example. The three-dimensional volume images may be created on the PACS workstation 110, in the three-dimensional subtraction application 130, or on a separate post-processing application, among other things. In an embodiment, a software generation routine may be used to create three-dimensional volume images.

Next, at step 230, the current and selected historical three-dimensional volumes are registered using image registration techniques. One or more image registration techniques are used to properly convert the current image captured by the medical imaging device 150 and align the current image with the selected historical image so as to prepare the image sets for three-dimensional subtraction. The one or more image registration techniques used to convert and align the image sets depend on the examination performed and the radiologist or other healthcare professional's choice (or a default setting in the advanced post-processing application). Image registration techniques are important to appropriately align the selected historical image with the current image. The one or more image registration techniques match points on the current image with points on the selected historical image. Image registration techniques may use extrinsic methods, intrinsic methods, and non-image based methods, for example. In an embodiment, a software registration routine may be used to perform the image registration techniques.

Then, at step 240, the current and selected historical three-dimensional volumes are subtracted using a three-dimensional subtraction application 130. The three-dimensional subtraction application 130 is used to create a three-dimensional subtracted image (or set of images) by subtracting common image data (e.g. bone) from two or more compared three-dimensional images. For example, a radiologist or other medical personnel may want to track changes in a patient's tumor. A current image of the tumor may be used with a historical image of the tumor in a three-dimensional subtraction application 130. The three-dimensional subtraction application 130 may create an image (or set of images) based on the differences between the current image (or set of images) and the historical image (or set of images), for example. The three-dimensional subtracted image (or set of images) may then show the difference between the current image of the tumor and the historical image of the tumor, among other things. A radiologist or other medical personnel may then use the three-dimensional subtracted image (or set of images) to track the changes in a patient's tumor or to make a diagnosis, for example. In an embodiment, a software construction routine may be used to construct the three-dimensional subtracted image (or set of images).

At step 250, the newly constructed three-dimensional subtracted volumes are displayed on the PACS workstation 110. In an embodiment, a software display routine may be used to display the three-dimensional subtracted volume image (or set of images) on the PACS workstation 110). The three-dimensional subtracted volumes may also be automatically saved to the historical images archive 140, the PACS workstation 110, and/or the three-dimensional subtraction application, among other things. A user may also manually save the images. Once the three-dimensional subtracted volume images are displayed on the PACS workstation 110, a user may view the images and/or perform further post-processing, for example, using the PACS workstation 110 and/or using a post-processing application, among other things.

Thus, certain embodiments accelerate the user's workflow and increase a user's productivity by using three-dimensional subtraction in a PACS to diagnose and track a patient's medical condition. Increased productivity includes a speed in which a diagnosis and tracking may be performed and an accuracy of reports produced based on the diagnosis and tracking.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A system for medical diagnosis and tracking, comprising:
    at least one medical imaging device adapted to create at least one current image from a current examination;
    a historical images archive adapted to storing at least one of:
        said at least one current image, and
        at least one historical image from a previous examination;
    a rules engine adapted to apply at least one rule to select at least one historical image for three-dimensional subtraction with said at least one current image;
    a three-dimensional subtraction application adapted to create at least one three-dimensional subtracted image by performing three-dimensional subtraction on said at least one current image and said at least one historical image, wherein said at least one current image and said at least one historical image do not contain contrast; and
    a Picture Archiving Communication System (PACS) workstation adapted to display said at least one three-dimensional subtracted image.

2. The system of claim 1, wherein said at least one rule is at least one of:
    a predefined rule, and
    a rule created dynamically by a user of said system for medical diagnosis and tracking.

3. The system of claim 1, wherein said at least one rule is defined by at least one of:
    software,
    a user, and
    a system administrator.

4. The system of claim 1, wherein said system is used for tumor diagnosis and tracking.

5. The system of claim 1, wherein said historical images archive, said rules engine, and said three-dimensional subtraction application are integrated on the Picture Archiving Communication System (PACS) workstation.

6. The system of claim 1, wherein said three-dimensional subtraction application uses image registration techniques to align said at least one current image and said at least one historical image before creating said at least one three-dimensional subtracted image.

7. A method for medical diagnosis and tracking, the method comprising:
    at least one processing device for performing at least:
        receiving at least one current medical image from a current examination;
        applying at least one rule for selecting at least one historical image from a previous examination for three-dimensional subtraction with said at least one current image from said current examination;

generating at least one current three-dimensional volume image using said at least one current medical image;

generating at least one historical three-dimensional volume image using said at least one historical image;

registering said at least one current three-dimensional volume image and said at least one historical three-dimensional volume image using image registration techniques;

constructing at least one three-dimensional subtracted image from said registered at least one current three-dimensional volume image and said at least one historical three-dimensional volume image, wherein said at least one current three-dimensional volume image and said at least one historical three-dimensional volume image do not contain contrast; and displaying said at least one three-dimensional subtracted image on a Picture Archiving Communication System (PACS) workstation.

8. The method of claim 7, wherein said at least one rule is at least one of:
   a predefined rule, and
   a rule created dynamically by a user of said system for medical diagnosis and tracking.

9. The method of claim 7, wherein said at least one rule is defined by at least one of:
   software,
   a user, and
   a system administrator.

10. The method of claim 7, wherein said medical imaging device uses at least one of:
    an X-ray imaging technique,
    a Computer Tomography (CT) imaging technique,
    a Medical Resonance Imaging (MRI) technique,
    a nuclear medicine imaging technique, and
    an ultrasound imaging technique.

11. The method of claim 7, wherein said at least one current image and said at least on historical image are at least one two-dimensional image slice.

12. The method of claim 7, wherein said at least one image registration technique includes at least one of:
    at least one extrinsic method,
    at least one intrinsic method, and
    at least one non-image based method.

13. The method of claim 12, wherein said at least one intrinsic method includes at least one of:
    at least one landmark based registration method,
    at least one segmentation based registration method, and
    at least one voxel based property registration method.

14. The method of claim 7, wherein said method is used for tumor diagnosis and tracking.

15. The method of claim 7, wherein at least one of:
    said generating step, and
    said constructing step,
is automatic.

16. A non-transitory computer-readable storage medium including a set of instructions for a computer, the set of instructions comprising:
   a receiving routine for receiving at least one current image from a medical imaging device, wherein the at least one current image is from a current examination;
   a selection routine for applying at least one rule for selecting at least one historical image from a previous examination for three-dimensional subtraction with said at least one current image from said current examination;
   a generation routine for generating at least one current three-dimensional volume image using said at least one current image and generating at least one historical three-dimensional volume image using said at least one historical image;
   a registration routine for registering said at least one current three-dimensional volume image and said at least one historical three-dimensional volume image using image registration techniques;
   a construction routine for constructing at least one three-dimensional subtracted image from said registered at least one current three-dimensional volume image and said at least one historical three-dimensional volume image, wherein said at least one current three-dimensional volume image and said at least one historical three-dimensional volume image do not contain contrast; and
   a display routine for displaying said at least one three-dimensional subtracted image on a Picture Archiving Communication System (PACS) workstation.

* * * * *